US007501130B2

(12) United States Patent
Aoki et al.

(10) Patent No.: US 7,501,130 B2
(45) Date of Patent: *Mar. 10, 2009

(54) METHODS FOR TREATING MYOFASCIAL PAIN

(75) Inventors: K. Roger Aoki, Laguna Hill, CA (US); Michael W. Grayston, Irvine, CA (US); Steven R. Carlson, Laguna Niguel, CA (US); Judith M. Leon, Laguna Niguel, CA (US)

(73) Assignee: Allergan, Inc., Irvine, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 11/403,666

(22) Filed: Apr. 13, 2006

(65) Prior Publication Data

US 2006/0210589 A1 Sep. 21, 2006

Related U.S. Application Data

(60) Division of application No. 10/933,723, filed on Sep. 2, 2004, which is a division of application No. 08/627,118, filed on Apr. 3, 1996, now Pat. No. 6,974,578, which is a continuation of application No. 08/173,996, filed on Dec. 28, 1993, now abandoned.

(51) Int. Cl.
*A61K 39/08* (2006.01)
(52) U.S. Cl. ............... 424/236.1; 424/239.1; 424/247; 424/1; 514/12
(58) Field of Classification Search ............... None
See application file for complete search history.

(56) References Cited

U.S. PATENT DOCUMENTS

| | | | | |
|---|---|---|---|---|
| 2,373,454 | A | 4/1945 | Burny et al. ............. | 167/78 |
| 2,719,102 | A | 9/1955 | Baldwin ............. | 167/78 |
| 3,132,995 | A | 5/1964 | Berger et al. ............. | 167/78 |
| 4,234,566 | A | 11/1980 | Packman et al. | |
| 4,713,240 | A | 12/1987 | Wilkins et al. ............. | 424/92 |
| 4,720,494 | A | 1/1988 | Felger et al. | |
| 4,932,936 | A | 6/1990 | Dykstra et al. ............. | 604/51 |
| 5,053,005 | A | 10/1991 | Borodic ............. | 604/51 |
| 5,055,291 | A | 10/1991 | Lam et al. ............. | 424/85.91 |
| 5,055,302 | A | 10/1991 | Laties et al. ............. | 424/427 |
| 5,183,462 | A | 2/1993 | Borodic ............. | 604/51 |
| 5,437,291 | A | 8/1995 | Pasricha et al. | |
| 5,696,077 | A * | 12/1997 | Johnson et al. ............. | 514/2 |
| 5,766,605 | A * | 6/1998 | Sanders et al. ............. | 424/239.1 |
| 6,113,915 | A * | 9/2000 | Aoki et al. ............. | 424/236.1 |
| 6,333,037 | B1 * | 12/2001 | Aoki et al. ............. | 424/236.1 |
| 6,372,226 | B2 * | 4/2002 | Aoki et al. ............. | 424/236.1 |
| 6,500,436 | B2 * | 12/2002 | Donovan ............. | 424/239.1 |
| 6,623,742 | B2 * | 9/2003 | Voet ............. | 424/236.1 |
| 6,683,049 | B1 * | 1/2004 | Aoki et al. ............. | 514/2 |
| 6,887,476 | B2 * | 5/2005 | Aoki et al. ............. | 424/184.1 |
| 6,974,578 | B1 * | 12/2005 | Aoki et al. ............. | 424/239.1 |
| 6,986,893 | B2 * | 1/2006 | Aoki et al. ............. | 424/236.1 |
| 2004/0014663 | A1 | 1/2004 | Aoki et al. ............. | 514/12 |
| 2004/0126396 | A1 | 7/2004 | Aoki et al. ............. | 424/239.1 |
| 2004/0126397 | A1 | 7/2004 | Aoki et al. ............. | 424/239.1 |
| 2004/0151740 | A1 | 8/2004 | Aoki et al. ............. | 424/239.1 |
| 2005/0112146 | A1 | 5/2005 | Graham ............. | 424/239.1 |

FOREIGN PATENT DOCUMENTS

| WO | WO 94/00481 | 1/1994 |
|---|---|---|
| WO | WO 94/23922 | 6/1994 |
| WO | WO 94/15629 | 7/1994 |
| WO | WO9528171 | 10/1995 |
| WO | WO 9528171 | 10/1995 |

OTHER PUBLICATIONS

File Medline on STN. AN No. 89041231. Escobar et al. 'Myofascial Pain Syndrome,' Orthopaedic review, vol. 16, No. 10, pp. 708-713. Oct. 1987. Enterned into Medline Dec. 7, 1988. Abstract Only.*
File Medline on STN. AN No. 87023096. Simons D. G. 'Fibrositis/fibromyalgia: a form of myofascial trigger points?' The American journal of medicine, (Sep. 29, 1986) vol. 81, No. 3A, pp. 93-98. Entered Medline: Nov. 7, 1986. Abstract Only.*
File Medline on STN. An No. 89134424. Buckelew S P. 'Fibromyalgia: a rehabilitation approach. A review.' American journal of physical medicine & rehabilitiation / Association of Academic Physiatrists, (Feb. 1989) vol. 68, No. 1, pp. 37-42. Entered Medline: Apr. 3, 1989. Abstract Only.*
Price et al. A Comparative Study of Tear Secretion in Blepharospasm and Hemifacial Spasm Patients Treated With Botulinum Toxin. J. of Clin. Neuro-opthalmology. vol. 13, No. 1, pp. 67-71. 1993.*
File scisearch on STN. AN No. 93:162872. Price et al. 'A Comparative Study of Tear Secretion in Blepharospasm and Hemifacial Spasm Patients Treated With Botulinum Toxin', J. or Clin. Neuro-Opthalmology, vol. 13, No. 1, pp. 67-71. Mar. 1993.*
File Caplus on STN. DN No. 105:220509. Knight, D.E. 'Botulinum Toxin Types A, B and D Inhibit Catecholamine Secretion From Bovine Adrenal Medullary Cells', FEBS, Lett. vol. 207, No. 2, pp. 222-226.*
Kondo et al. 'Modification of the Action of Pentagastrin on Acid Secretion by Botulinum Toxin', Experientia. vol. 33, No. 6, pp. 750-751.*
Borodic, G.E., et al., "Botulinum B Toxin as an Alternative to Botulinum A Toxin: A Histologic Study," Ophtalmic Plastic and Reconstructive Surgery, vol. 9, No. 3, pp. 182-190.
Heneson, N., "Deadly toxin calms excited muscles," Science, 1990, p. 24.

(Continued)

*Primary Examiner*—Anish Gupta
(74) *Attorney, Agent, or Firm*—Claude L. Nassif; Stephen Donovan; Martin Voet

(57) ABSTRACT

A method and composition for treating a patient suffering from a disease, disorder or condition and associated pain include the administration to the patient of a therapeutically effective amount of a neurotoxin selected from a group consisting of Botulinum toxin types A, B, C, D, E, F and G.

2 Claims, No Drawings

OTHER PUBLICATIONS

Jankovic, J., et al., "Therapeutic Uses of Botulinum Toxin," The New England Journal of Medicine, Apr. 25, 1991, 1186-.

Schantz, E., et al., "Properties and Use of Botulinum Toxin and Other Microbial Neurotoxins in Medicine," Microbiological Reviews, Mar. 1992, pp. 80-99.

Sellin, L.C., et al., "Different effects of types A and B botulinum toxin on transmitter release at the rat neuromuscular junction," Acta Physiol Scan, 1983; 119:127-133.

Purngvarin et al; J. Med. Assoc. Thai. (Apr. 1992) 75 (4) 199-203.

Correspondence Dated Dec. 10, 1991 Between William C. Shepherd and Ira Sanders.

Correspondance Dated Apr. 13, 1992 Between Ira Sanders and Angelika S. Aswad Regarding "Animal Study".

Partial Correspondence Dated Apr. 24, 1992 Between Angelika S. Aswad and Dr. Sanders Regarding Botulinum Toxin to Decrease Salivary Flow.

Ambache, J. Physiol. (1951) 113, 1-17.

Brin. Arch. De Neurobiol. 54. Supl. 3 (7-23) 1991.

Bergmann, MD, et al.; Selective Degeneration of Sudomotor Fibers in Ross Syndrome and Successful Treatment of Compensatory Hyperhidrosis with Botulinum Toxin; *Muscle & Nerve*; Dec. 1998, pp. 1790-1793.

Glogau, Richard MD; Botulinum A Neurotoxin for Axillary Hyperhidrosis; *Dermatol Surg.*; Aug. 1998; 24(8), pp. 817-819.

Heneson, Nancy; Deadly Toxin Calms Excited Muscles; *New Scientist*, Dec. 8, 1990, p. 24.

Kaszynski, Edwin, et al.; Mouse Foot Screen for the Inhibition of Sweating by Anticholinergic Drugs; *The Journal of Investigative Dermatology*, 1974, vol. 62, pp. 510-513.

Naumann, M., et al.; Botulinum Toxin for Focal Hyperhidrosis: Technical Considerations and Improvements in Application; *British Journal of Dermatology*, 1998, 139, pp. 1123-1124.

Naumann, Markus, et al.; Botulinum Toxin for Palmar Hyperhidrosis; *Lancet*, Jan. 25, 1997, vol. 349.

Naumann, Markus, et al.; Focal Hyperhidrosis; *Arch Dermatol*, Mar. 1998, vol. 134, pp. 301-304.

Naver, Hans, et al.; The Treatment of Focal Hyperhidrosis with Botulinum Toxin; *European Journal of Neurology*, 1997, vol. 4, Suppl 2, pp. S75-S79.

Odderson, Ib, MD; Axillary Hyperhidrosis: Treatment with Botulinum Toxin A; *Arch Phys Med. Rehabil.*, Mar. 1998, vol. 79, pp. 350-352.

Schantz, Edward, et al.; Properties and Use of Botulinum Toxin and Other Microbial Neurotoxins in Medicine; *Microbiological Reviews*, Mar. 1992, pp. 80-95.

Schnider, P., et al.; Double-Blind Trial of Botulinum A Toxin for the Treatment of Focal Hypderhidrosis of the Palms; *British Journal of Dermatology*, 1997, 136(4), pp. 548-552.

Shelley, W. B., et al.; Botulinum Toxin Therapy for Palmar Hyperhidrosis; *Journal of the America Academy of Dermatology*, Feb. 1998, 38 (2 Part 1), pp. 227-229.

Stevens, Leslie M., et al., Development and Properties of the Secretory Response in Rat sweat Glands: Relationship to the Induction of Cholinergic Function in Sweat Gland Innervation; *Developmental Biology*, 1987, 123, pp. 179-190.

Grusser Von O-J, Die ersten systematischen Beschreibungen und tierexperiemtellen Untersuchungen des Botulisums, Sudhoffa Archiv (1986), 70(2), 167-186. English translation attached.

Kerner, J. Das Fettgift oder die fettsaure und ihre wirkungen auf den thierischen organismus, ein beytrag zur untersuchung des in verdorbenen wursten giftig wirkenden stoffes. Stuttgart und Tubingen: Cotta, 368 pages (1822); English translation of table of contents and of Chapter 8 enclosed.

\* cited by examiner

METHODS FOR TREATING MYOFASCIAL PAIN

CROSS REFERENCE

This application is a divisional of application Ser. No. 10/933,723, filed Sep. 2, 2004, which is a divisional application of application Ser. No. 08/627,118, filed Apr. 3, 1996 now U.S. Pat. No. 6,974,578, which is a continuation of application Ser. No. 08/173,996, filed Dec. 28, 1993, now abandoned. The disclosures of all of these prior applications are incorporated herein by reference in all their entireties.

FIELD OF THE INVENTION

The present invention provides novel methods for treating various disorders and conditions, with Botulinum toxins. Importantly, the present invention provides methods useful in relieving pain related to muscle activity or contracture and therefore is of advantage in the treatment of, for example, muscle spasm such as Temporomandibular Joint Disease, low back pain, myofascial pain, pain related to spasticity and dystonia, as well as sports injuries, and pain related to contractures in arthritis.

BACKGROUND OF THE INVENTION

Heretofore, Botulinum toxins, in particular Botulinum toxin type A, has been used in the treatment of a number of neuromuscular disorders and conditions involving muscular spasm; for example, strabismus, blepharospasm, spasmodic torticollis (cervical dystonia), oromandibular dystonia and spasmodic dysphonia (laryngeal dystonia). The toxin binds rapidly and strongly to presynaptic cholinergic nerve terminals and inhibits the exocytosis of acetylcholine by decreasing the frequency of acetylcholine release. This results in local paralysis and hence relaxation of the muscle afflicted by spasm.

For one example of treating neuromuscular disorders, see U.S. Pat. No. 5,053,005 to Borodic, which suggests treating curvature of the juvenile spine, i.e., scoliosis, with an acetylcholine release inhibitor, preferably Botulinum toxin A.

For the treatment of strabismus with Botulinum toxin type A, see Elston, J. S., et al., *British Journal of Ophthalmology*, 1985, 69, 718-724 and 891-896. For the treatment of blepharspasm with Botulinum toxin type A, see Adenis, J. P., et al., *J. Fr. Ophthalmol.*, 1990, 13 (5) at pages 259-264. For treating squint, see Elston, J. S., *Eye*, 1990, 4(4):VII. For treating spasmodic and oromandibular dystonia torticollis, see Jankovic et al., *Neurology*, 1987, 37, 616-623.

Spasmodic dysphonia has been treated with Botulinum toxin type A. See Blitzer et al., *Ann. Otol. Rhino. Laryngol*, 1985, 94, 591-594. Lingual dystonia was treated with Botulinum toxin type A according to Brin et al., *Adv. Neurol.* (1987) 50, 599-608. Finally, Cohen et al., *Neurology* (1987) 37 (Suppl. 1), 123-4, discloses the treatment of writer's cramp with Botulinum toxin type A.

The term Botulinum toxin is a generic term embracing the family of toxins produced by the anaerobic bacterium Clostridium botulinum and, to date, seven immunologically distinct neurotoxins have been identified. These have been given the designations A, B, C, D, E, F and G. For further information concerning the properties of the various Botulinum toxins, reference is made to the article by Jankovic and Brin, *The New England Journal of Medicine*, No. 17, 1990, pp. 1186-1194, and to the review by Charles L. Hatheway in Chapter 1 of the book entitled *Botulinum Neurotoxin and Tetanus Toxin*, L. L. Simpson, Ed., published by Academic Press Inc. of San Diego, Calif., 1989, the disclosures in which are incorporated herein by reference.

The neurotoxic component of Botulinum toxin has a molecular weight of about 150 kilodaltons and is thought to comprise a short polypeptide chain of about 50 kD which is considered to be responsible for the toxic properties of the toxin, i.e., by interfering with the exocytosis of acetylcholine, by decreasing the frequency of acetylcholine release, and a larger polypeptide chain of about 100 kD which is believed to be necessary to enable the toxin to bind to the presynaptic membrane.

The "short" and "long" chains are linked together by means of a simple disulfide bridge. (It is noted that certain serotypes of Botulinum toxin, e.g., type E, may exist in the form of a single chain un-nicked protein, as opposed to a dichain. The single chain form is less active but may be converted to the corresponding dichain by nicking with a protease, e g., trypsin. Both the single and thin dichain are useful in the method of the present invention.)

In general, four physiologic groups of *C. botulinum* are recognized (I, II, III, IV). The organisms capable of producing a serologically distinct toxin may come from more than one physiological group. For example, Type B and F toxins can be produced by strains from Group I or II. In addition, other strains of clostridial species (*C. baratii*, type F; *C. butyricum*, type E; *C. novyi*, type $C_1$ or D) have been identified which can produce botulinum neurotoxins.

Immunotoxin conjugates of ricin and antibodies, which are characterized as having enhanced cytotoxicity through improving cell surface affinity, are disclosed in European Patent Specification 0 129 434. The inventors note that botulinum toxin may be utilized in place of ricin.

Botulinum toxin is obtained commercially by establishing and growing cultures of *C. botulinum* in a fermenter and then harvesting and purifying the fermented mixture in accordance with known techniques.

Botulinum toxin type A, the toxin type generally utilized in treating neuromuscular conditions, is currently available commercially from several sources; for example, from Porton Products Ltd. UK, under the trade name "DYSPORT," and from Allergan, Inc., Irvine, Calif., under the trade name BOTOX®.

It is one object of the invention to provide novel treatments of neuromuscular disorders and conditions with various Botulinum toxin types. It is another object of the present invention to relieve pain with various Botulinum toxin types.

SUMMARY OF THE INVENTION

The present invention provides a method for relieving pain, associated with muscle contractions, a composition and a method of treating conditions such as cholinergic controlled secretions including excessive sweating, lacrimation and mucus secretions and a method for treating smooth muscle disorders including, but not limited to, spasms in the sphincter of the cardiovascular arteriole, gastrointestinal system, urinary, gall bladder and rectum, which method comprises administering to the patient suffering from said disorder or condition a therapeutically effective amount of Botulinum toxin selected from the group consisting of Botulinum toxin types B, C, D, E, F and G.

Each serotype of Botulinum toxin has been identified as immunologically different proteins through the use of specific antibodies. For example, if the antibody (antitoxin) recognizes, that is, neutralizes the biological activity of, for example, type A it will not recognize types B, C, D, E, F or G.

While all of the Botulinum toxins appear to be zinc endopeptidases, the mechanism of action of different serotypes, for example, A and E within the neuron appear to be different than that of Type B. In addition, the neuronal surface "receptor" for the toxin appears to be different for the serotypes.

In the area of use of the Botulinum toxins in accordance with the present invention with regard to organ systems which involve the release of neurotransmitter, it is expected to introduce the toxins A, B, C, D, E, F, and G directly by local injections.

DETAILED DESCRIPTION

The Botulinum toxins used according to the present invention are Botulinun toxins type A, B, C, D, E, F and G.

The physiologic groups of *Clostridium botulinum* types are listed in Table I.

TABLE 1

Physiologic Groups of *Clostridium botulinum*

| Group | Toxin Sero-Type | Biochemistry | Milk Digest | Glucose Fermentation | Lipase | Phages & Plasmids | Phenotypically Related Clostridium (nontoxigenic) |
|---|---|---|---|---|---|---|---|
| I | A, B, F | Proteolytic saccharolytic | + | + | + | + | *C. sporogenes* |
| II | B, E, F | Nonproteolytic saccarolytic psychotrophic | − | + | + | + | |
| III | C, D | Nonproteolytic saccarolytic | ± | + | + | + | *C. novvi* |
| IV | G | Proteolytic nonsaccarolytic | + | − | − | − | *C. subterminale* |

These toxin types may be produced by selection from the appropriate physiologic group of *Clostridium botulinum* organisms. The organisms designated as Group I are usually referred to as proteolytic and produce Botulinum toxins of types A, B and F. The organisms designated as Group II are saccharolytic and produce Botulinum toxins of types B, E and F. The organisms designated as Group III produce only Botulinum toxin types C and D and are distinguished from organisms of Groups I and II by the production of significant amounts of propionic acid. Group IV organisms only produce neurotoxin of type G. The production of any and all of the Botulinum toxin types A, B, C, D, E, F and G are described in Chapter 1 of *Botulinun Neurotoxin and Tetanus Toxin*, cited above, and/or the references cited therein. Botulinum toxins types B, C, D, E, F and G are also available from various species of clostridia.

Currently fourteen species of clostridia are considered pathogenic. Most of the pathogenic strains produce toxins which are responsible for the various pathological signs and symptoms. Organisms which produce Botulinum toxins have been isolated from botulism outbreaks in humans (types A, B, E and F) and animals (types C and D). Their identities were described through the use of specific antitoxins (antibodies) developed against the earlier toxins. Type G toxin was found in soil and has low toxigenicity. However, it has been isolated from autopsy specimens, but thus far there has not been adequate evidence that type G botulism has occurred in humans.

Preferably, the toxin is administered by means of intramuscular injection directly into a local area such as a spastic muscle, preferably in the region of the neuromuscular junction, although alternative types of administration (e.g., subcutaneous injection), which can deliver the toxin directly to the affected region, may be employed where appropriate. The toxin can be presented as a sterile pyrogen-free aqueous solution or dispersion and as a sterile powder for reconstitution into a sterile solution or dispersion.

Where desired, tonicity adjusting agents such as sodium chloride, glycerol and various sugars can be added. Stabilizers such as human serum albumin may also be included. The formulation may be preserved by means of a suitable pharmaceutically acceptable preservative such as a paraben, although preferably it is unpreserved.

It is preferred that the toxin is formulated in unit dosage form; for example, it can be provided as a sterile solution in a vial or as a vial or sachet containing a lyophilized powder for reconstituting a suitable vehicle such as saline for injection.

In one embodiment, the Botulinum toxin is formulated in a solution containing saline and pasteurized human serum albumin, which stabilizes the toxin and minimizes loss through non-specific adsorption. The solution is sterile filtered (0.2 micron filter), filled into individual vials and then vacuum-dried to give a sterile lyophilized powder. In use, the powder can be reconstituted by the addition of sterile unpreserved normal saline (sodium chloride 10 0.9% for injection).

The dose of toxin administered to the patient will depend upon the severity of the condition; e.g., the number of muscle groups requiring treatment, the age and size of the patient and the potency of the toxin. The potency of the toxin is expressed as a multiple of the $LD_{50}$ value for the mouse, one unit (U) of toxin being defined as being the equivalent to that amount, on a per mouse basis, that kills 50% of a group of Swiss-Webster mice weighing between 17 and 22 grams each.

The dosages used in human therapeutic applications are roughly proportional to the mass of muscle being injected. Typically, the dose administered to the patient may be up from about 0.01 to about 1,000 units; for example, up to about 500 units, and preferably in the range from about 80 to about 460 units per patient per treatment, although smaller of larger doses may be administered in appropriate circumstances such as up to about 50 units for the relief of pain and in controlling cholinergic secretions.

As the physicians become more familiar with the use of this product, the dose may be changed. In the Botulinum toxin type A, available from Porton, DYSPORT, 1 nanogram (ng) contains 40 units. 1 ng of the Botulinum toxin type A, available from Allergan, Inc., i.e., BOTOX®, contains 4 units. The potency of Botulinum toxin and its long duration of action mean that doses will tend to be administered on an infrequent basis. Ultimately, however, both the quantity of toxin administered and the frequency of its administration will be at the discretion of the physician responsible for the treatment and will be commensurate with questions of safety and the effects produced by the toxin.

In some circumstances, particularly in the relief of pain associated with sports injuries, such as, for example, charleyhorse, botulinum type F, having a short duration activity, is preferred.

The invention will now be illustrated by reference to the following nonlimiting examples.

In each of the examples, appropriate areas of each patient are injected with a sterile solution containing the confirmation of Botulinum toxin. Total patient doses range from about 0.01 units to 460 units. Before injecting any muscle group, careful consideration is given to the anatomy of the muscle group, the aim being to inject the area with the highest concentration of neuromuscular junctions, if known. Before injecting the muscle, the position of the needle in the muscle is confined by putting the muscle through its range of motion and observing the resultant motion of the needle end. General anaesthesia, local anaesthesia and sedation are used according to the age of the patient, the number of sites to be injected, and the particular needs of the patient. More than one injection and/or sites of injection may be necessary to achieve the desired result. Also, some injections, depending on the muscle to be injected, may require the use of fine, hollow, Teflon-coated needles, guided by electromyography.

Following injection, it is noted that there are no systemic or local side effects and none of the patients are found to develop extensive local hypotonicity. The majority of patients show an improvement in function both subjectively and when measured objectively.

EXAMPLE 1

The Use of Botulinum Toxin Types B to G in the Treatment of Tardive Dyskinesia

A male patient, age 45, suffering from tardive dyskinesia resulting from the treatment with an antipsychotic drug, such as Thorazine or Haldol, is treated with 150 units of Botulinum toxin type B by direct injection of such toxin into the facial muscles. After 1-3 days, the symptoms of tardive dyskinesia, i.e., orofacial dyskinesia, athetosis, dystonia, chorea, tics and facial grimacing, etc. are markedly reduced.

EXAMPLE 1(a)

The method of Example 1 is repeated, except that a patient suffering from tardive dyskinesia is injected with 50-200 units of Botulinum toxin type C. A similar result is obtained.

EXAMPLE 1(b)

The method of Example 1 is repeated, except that a patient suffering from tardive dyskinesia is injected with 50-200 units of Botulinum toxin type D. A similar result is obtained.

EXAMPLE 1(c)

The method of Example 1 is repeated, except that a patient suffering from tardive dyskinesia is injected with 50-200 units of Botulinum toxin type E. A similar result is obtained.

EXAMPLE 1(d)

The method of Example 1 is repeated, except that a patient suffering from tardive dyskinesia is injected with 50-200 units of Botulinum toxin type F. A similar result is obtained.

EXAMPLE 1(e)

The method of Example 1 is repeated, except that 25 a patient suffering from tardive dyskinesia is injected with 50-200 units of Botulinum toxin type G. A similar result is obtained.

EXAMPLE 2

The Use of Botulinum Toxin Types B to G in the Treatment of Spasmodic Torticollis A male, age 45, suffering from spasmodic torticollis, as manifested by spasmodic or tonic contractions of the neck musculature, producing stereotyped abnormal deviations of the head, the chin being rotated to one side, and the shoulder being elevated toward the side at which the head is rotated, is treated by injection with 100-1,000 units of Botulinum toxin type E. After 3-7 days, the symptoms are substantially alleviated; i.e., the patient is able to hold his head and shoulder in a normal position.

EXAMPLE 2(a)

The method of Example 2 is repeated, except that a patient suffering from spasmodic torticollis is injected with 100-1,000 units of Botulinum toxin type B. A similar result is obtained.

EXAMPLE 2(b)

The method of Example 2 is repeated, except that a patient suffering from spasmodic torticollis is injected with 100-1,000 units of Botulinum toxin type C. A similar result is obtained.

EXAMPLE 2(c)

The method of Example 2 is repeated, except that a patient suffering from spasmodic torticollis is injected with 100-1,000 units of Botulinum toxin type D. A similar result is obtained.

EXAMPLE 2(d)

The method of Example 2 is repeated, except that a patient suffering from spasmodic torticollis is injected with 100-1,000 units of Botulinum toxin type E. A similar result is obtained.

EXAMPLE 2(e)

The method of Example 2 is repeated, except that a patient suffering from spasmodic torticollis is injected with 100-1,000 units of Botulinum toxin type F. A similar result is obtained.

EXAMPLE 2(f)

The method of Example 2 is repeated, except that a patient suffering from spasmodic torticollis is injected with 100-1,000 units of Botulinum toxin type G. A similar result is obtained.

EXAMPLE 3

The Use of Botulinum Toxin Types B to G in the Treatment of Essential Tremor A male, age 45, suffering from essential tremor, which is manifested as a rhythmical oscillation of head or hand muscles and is provoked by maintenance of posture or movement, is treated by injection with 50-1,000 units of Botulinum toxin type B. After two to eight weeks, the symptoms are substantially alleviated; i.e., the patient's head or hand ceases to oscillate.

EXAMPLE 3(a)

The method of Example 3 is repeated, except that a patient suffering from essential tremor is injected with 100-1,000 units of Botulinum toxin type C. A similar result is obtained.

EXAMPLE 3(b)

The method of Example 3 is repeated, except that a patient suffering from essential tremor is injected with 100-1,000 units of Botulinum toxin type D. A similar result is obtained.

EXAMPLE 3(c)

The method of Example 3 is repeated, except that a patient suffering from essential tremor is injected with 100-1,000 units of Botulinum toxin type B. A similar result is obtained.

EXAMPLE 3(d)

The method of Example 3 is repeated, except that a patient suffering from essential tremor is injected with 100-1,000 units of Botulinum toxin type F. A similar result is obtained.

EXAMPLE 3(e)

The method of Example 3 is repeated, except that a patient suffering from essential tremor is injected with 100-1,000 units of Botulinum toxin type G. A similar result is obtained.

EXAMPLE 4

The Use of Botulinum Toxin Types B to G in the Treatment of Spasmodic Dysphonia A male, age 45, unable to speak clearly, due to spasm of the vocal chords, is treated by injection of the vocal chords with Botulinum toxin type B, having an activity of 80-500 units. After 3-7 days, the patient is able to speak clearly.

EXAMPLE 4(a)

The method of Example 4 is repeated, except that a patient suffering from spasmodic dysphonia is injected with 80-500 units of Botulinum toxin type C. A similar result is obtained.

EXAMPLE 4(b)

The method of Example 4 is repeated, except that a patient suffering from spasmodic dysphonia is injected with 80-500 units of Botulinum toxin type D. A similar result is obtained.

EXAMPLE 4(c)

The method of Example 4 is repeated, except that a patient suffering from spasmodic dysphonia is injected with 80-500 units of Botulinum toxin type E. A similar result is obtained.

EXAMPLE 4(d)

The method of Example 4 is repeated, except that a patient suffering from spasmodic dysphonia is injected with 80-500 units of Botulinum toxin type F. A similar result is obtained.

EXAMPLE 4(e)

The method of Example 4 is repeated, except that a patient suffering from spasmodic dysphonia is injected with 8-500 units of Botulinum toxin type G. A similar result is obtained.

EXAMPLE 5

The Use of Botulinum Toxin Types A-G in the Treatment of Excessive Sweating, Lacrimation or Mucus Secretion or Other Cholinergic Controlled Secretions A male, age 65, with excessive unilateral sweating is treated by administering 0.01 to 50 units, of Botulinum toxin, depending upon degree of desired effect. The larger the dose, usually the greater spread and duration of effect. Small doses are used initially. Any serotype toxin alone or in combination could be used in this indication. The administration is to the gland nerve plexus, ganglion, spinal cord or central nervous system to be determined by the physician's knowledge of the anatomy and physiology of the target glands and secretary cells. In addition, the appropriate spinal cord level or brain area can be injected with the toxin (although this would cause many effects, including general weakness). Thus, the gland (if accessible) or the nerve plexus or ganglion are the targets of choice. Excessive sweating, tearing (lacrimation), mucus secretion or gastrointestinal secretions are positively influenced by the cholinergic nervous system. Sweating and tearing are under greater cholinergic control than mucus or gastric secretion and would respond better to toxin treatment. However, mucus and gastric secretions could be modulated through the cholinergic system. All symptoms would be reduced or eliminated with toxin therapy in about 1-7 days. Duration would be weeks to several months.

EXAMPLE 6

The Use of Botulinum Toxin Types A-G in the Treatment of Muscle Spasms in Smooth Muscle Disorders Such As Sphincters of the Cardiovascular Arteriole, Gastrointestinal System. Urinary or Gall Bladder, Rectal. Etc.

A male, age 30-40, with a constricted pyloric valve which prevents his stomach from emptying, is treated by administering 1-50 units of Botulinum toxin. The administration is to the pyloric valve (which controls release of stomach contents into the intestine) divided into 2 to 4 quadrants, injections made with any endoscopic device or during surgery. In about 1-7 days, normal emptying of the stomach, elimination or drastic reduction in regurgitation occurs.

EXAMPLE 7

The Use of Botulinum Toxin Types A-G in the Treatment of Muscle Spasms and Control of Pain Associated with Muscle Spasms in Temporal Mandibular Joint Disorders A female, age 35, is treated by administration of 0.1 to 50 units total of Botulinum toxin. The administration is to the muscles controlling the closure of the jaw. Overactive muscles may be identified with ENG (electromyography) guidance. Relief of pain associated with muscle spasms, possible reduction in jaw clenching occurs in about 1-3 days.

EXAMPLE 8

The Use of Botulinum Toxin Types A-G in the Treatment of Muscle Spasms and Control of Pain Associated with Muscle Spasms in Conditions Secondary to Sports Injuries (Charleyhorse)

A male, age 20, with severe cramping in thigh after sports injury is treated by administration of a short duration toxin, possible low dose (0.1-25 units) of preferably type F to the muscle and neighboring muscles which are in contraction ("cramped"). Relief of pain occurs in 1-7 days.

EXAMPLE 9

The Use of Botulinum Toxin Types A-G in the Treatment of Muscle Spasms and Control of Pain Associated with Muscle Spasms in Smooth Muscle Disorders Such as Gastrointestinal Muscles A female, age 35, with spastic colitis, is treated with 1-100 units of botulinum toxin divided into several areas, enema (1-5 units) delivered in the standard enema volume, titrate dose, starting with the lowest dose. Injection is to the rectum or lower colon or a low dose enema may be employed. Cramps and pain associated with spastic colon are relieved in 1-10 days.

EXAMPLE 10

The Use of Botulinum Toxin Types A-G in the Treatment of Muscle Spasms and Control of Pain Associated with Muscle Spasms in Spasticity Conditions Secondary to Stroke, Traumatic Brain or Spinal Cord Injury A male, age 70, post-stroke or cerebral vascular event, is injected with 50 to 300 units of Botulinum toxin in the major muscles involved in severe closing of hand and curling of wrist and forearm or the muscles involved in the closing of the legs such that the patient and attendant have difficulty with hygiene. Relief of these symptoms occurs in 7 to 21 days.

EXAMPLE 11

The Use of Botulinum Toxin Types A-G in the Treatment of Patients with Swallowing Disorders A patient with a swallowing disorder caused by excessive throat muscle spasms is injected with about 1 to about 300 units of Botulinum toxin in the throat muscles. Relief the swallowing disorder occurs in about 7 to about 21 days.

EXAMPLE 12

The Use of Botulinum toxin Types A-G in the Treatment of Patients with Tension Headache A patient with a tension headache caused by excessive throat muscle spasms is injected with about 1 to about 300 units of Botulinum toxin in muscles of the head and upper neck. Relief of the tension headache occurs in about 1 to about 7 days.

Although there has been hereinabove described a use of Botulinum toxins for treating various disorders, conditions and pain, in accordance with the present invention, for the purpose of illustrating the manner in which the invention may be used to advantage, it should be appreciated that the invention is not limited thereto since many obvious modifications can be made, and it is intended to include within this invention any such modifications as will fall within the scope of the appended claims. Accordingly, any and all modifications, variations, or equivalent arrangements which may occur to those skilled in the art, should be considered to be within the scope of the present invention as defined in the appended claims.

What is claimed is:

1. A method for treating myofascial pain in a patient in need thereof, the method comprising the step of intramuscularly administering to the patient an effective amount of a botulinum toxin type A, wherein the patient is administered at least about 50 units of the botulinum toxin type A, the botulinum toxin type A providing myofascial pain relief, thereby treating myofascial pain of the patient.

2. A method for treating myofascial pain in a patient in need thereof, the method comprising the step of intramuscularly administering to the patient an effective amount of a botulinum toxin type A, wherein the patient is administered at least about 1000 units of the botulinum toxin type A, the botulinum toxin type A providing myofascial pain relief, thereby treating myofascial pain of the patient.

* * * * *

UNITED STATES PATENT AND TRADEMARK OFFICE
CERTIFICATE OF CORRECTION

PATENT NO. : 7,501,130 B2
APPLICATION NO. : 11/403666
DATED : March 10, 2009
INVENTOR(S) : K. Roger Aoki et al.

It is certified that error appears in the above-identified patent and that said Letters Patent is hereby corrected as shown below:

On the title page, under "Foreign Patent Documents", column 2, line 2, delete "WO 94/23922" and insert -- WO 94/28922 --, therefor.

On the title page, under "Other Publications", column 2, line 3, delete "Enterned" and insert -- Entered --, therefor.

On the title page, under "Other Publications", column 2, line 10, delete "rehabilitiation" and insert -- rehabilitation --, therefor.

On the title page, under "Other Publications", column 2, line 18, delete "J. or" and insert -- J. of --, therefor.

On the title page, under "Other Publications", column 2, line 20, delete "DN" and insert -- AN --, therefor.

On page 2, under "Other Publications", column 1, line 12, delete "Correspondance" and insert -- Correspondence --, therefor.

On page 2, column 2, line 15, delete "Hypderhidrosis" and insert -- Hyperhidrosis --, therefor.

In column 1, line 45-46, delete "blepharspasm" and insert -- blepharospasm --, therefor.

In column 2, line 18, delete "e g.," and insert -- e.g., --, therefor.

In column 2, line 19, delete "thin" and insert -- the --, therefor.

In column 3, line 16, delete "Botulinun" and insert -- Botulinum --, therefor.

In column 3, line 18, delete "Table I." and insert -- Table 1. --, therefor.

In column 3, under Table 1, line 9, delete "saccarolytic" and insert -- saccharolytic --, therefor.

In column 3, under Table 1, line 12, delete "saccarolytic" and insert -- saccharolytic --, therefor.

UNITED STATES PATENT AND TRADEMARK OFFICE
CERTIFICATE OF CORRECTION

PATENT NO. : 7,501,130 B2
APPLICATION NO. : 11/403666
DATED : March 10, 2009
INVENTOR(S) : K. Roger Aoki et al.

It is certified that error appears in the above-identified patent and that said Letters Patent is hereby corrected as shown below:

In column 3, under Table 1, line 14, delete "nonsaccarolytic" and insert -- nonsaccharolytic --, therefor.

In column 3, line 49, delete "Botulinun" and insert -- Botulinum --, therefor.

Signed and Sealed this

Nineteenth Day of May, 2009

JOHN DOLL
*Acting Director of the United States Patent and Trademark Office*